US00PP22191P2

(12) United States Plant Patent
Dozier, Jr. et al.

(10) Patent No.: US PP22,191 P2
(45) Date of Patent: Oct. 11, 2011

(54) KIWI PLANT NAMED 'AU GOLDEN DRAGON'

(50) Latin Name: ***Actinidia chinensis* Planch**
Varietal Denomination: AU Golden Dragon

(75) Inventors: William Alfred Dozier, Jr., Opelika, AL (US); Bryan Shelton Wilkins, LaFayette, AL (US); Jim Pitts, Clanton, AL (US); Curtis Jay Hansen, Opelika, AL (US); Floyd M. Woods, Auburn, AL (US); James D. Spiers, Auburn, AL (US); Qinghong Chen, Wuhan (CN); Zhongqi Qin, Wuhan (CN); Yingchun Jiang, Wuhan (CN); Xia Gu, Wuhan (CN); Aichun Xu, Wuhan (CN)

(73) Assignee: Auburn University, Auburn, AL (US)

( * ) Notice: Subject to any disclaimer, the term of this patent is extended or adjusted under 35 U.S.C. 154(b) by 0 days.

(21) Appl. No.: 12/711,219

(22) Filed: Feb. 23, 2010

(51) Int. Cl.
*A01H 5/00* (2006.01)

(52) U.S. Cl. ..... Plt./156

(58) Field of Classification Search ..... Plt./156
See application file for complete search history.

(56) References Cited

OTHER PUBLICATIONS

Wall et al. "Vegetative and Floral Chilling Requirement of Four New Kiwi Cultivars of *Actinidia chinensis* and *A. deliciosa*," (HortScience 43(3):644-647, Jun. 2008.*

Wall et al. "Determining a Maturity Index and the Effect of Chilling Requirements, and Cytokinin Application on Three New Kiwi Cultivars," Thesis—Degree of Master of Science, Auburn University, Aug. 2006, 87 pages.*

* cited by examiner

*Primary Examiner* — Susan McCormick Ewoldt
(74) *Attorney, Agent, or Firm* — Andrus, Sceales, Starke & Sawall, LLP

(57) ABSTRACT

A new and distinct cultivar of the species *Actinidia chinesis* Planch is described. 'AU Golden Dragon' has a low chilling requirement, fruit is very early maturing, excellent flavor with a non acid sweet taste, and high soluble solids and dry matter content. 'AU Golden Dragon' matures about 50 days ahead of 'Hort 16A' (patented), the industry standard for golden flesh kiwi, therefore, the two cultivars will not compete in the market place. 'AU Golden Dragon' fruit quality indices are similar to fruit quality indices of 'Hort 16A' (patented). There have been no differences in plant performance and fruit quality of 'AU Golden Dragon' plants grown in China and Central Alabama.

6 Drawing Sheets

Latin name of the genus and species of the plant claimed: *Actinidia chinensis* Planch.

Variety denomination: 'AU GOLDEN DRAGON'.

RELATED APPLICATIONS

U.S. patent application Ser. No. 12/711,204, filed on Feb. 23, 2010, and entitled "KIWI PLANT NAMED 'AU GOLDEN TIGER'" and U.S. patent application Ser. No. 12/711,194, filed on Feb. 23, 2010, and entitled "KIWI PLANT NAMED 'AU GOLDEN SUNSHINE'" are both incorporated by reference herein. "AU Golden Tiger' is the male pollenizer used with "AU Golden Sunshine'. 'AU Golden Sunshine' is a female variety used as a companion and as a comparison cultivar with 'AU Golden Dragon'.

BACKGROUND OF THE INVENTION

Seed were collected from fruit produced by open pollinated and unnamed kiwi plants of *Actinidia chinensis* Planch growing in a cultivated area of Fang County Hubei Province of P.R. China. Seedlings developed from the collected seeds were planted and grown in an experimental orchard and evaluated for fruit quality parameters, maturity date, flesh color and appearance. 'AU Golden Dragon' was selected as a potential commercial cultivar from this experimental evaluation planting because of its excellent plant performance, earliness of maturity and fruit quality, fragrance and yield.

'AU Golden Dragon' has the best fruit quality and performance of the very early maturing cultivars of *Actinidia chinensis* Planch. The new cultivar is able to be asexually reproduced by softwood and hardwood rooted cuttings or by budding or grafting onto a seedling or rooted cutting grown rootstock with the unique characteristics being transferred through succeeding asexual propagations. In China 'AU Golden Dragon' was vegetatively propagated by grafting and planted for evaluation in experimental plantings in Shanghui, Jiangsu, Fusion and Shanxi provinces. 'AU Golden Dragon' was vegetatively propagated by softwood and hardwood cuttings and cleft grafting for evaluation in experimental plantings in Central Alabama. This cultivar has had excellent and equal performance in both China and Alabama test locations. The fruit of 'AU Golden Dragon' is elliptical in shape with a brown smooth skin, very early maturity, excellent flavor with a non acid sweet taste, and high soluble solids and percent dry matter content.

SUMMARY OF THE INVENTION

The present invention relates to a new and distinct low chilling requirement yellow fleshed kiwi cultivar of *Actinidia chinensis* Planch that produces elliptical shaped fruit that ripens very early in the kiwi ripening season. The fruit skin is brown with short tomentose hairs. The fruit have high soluble solids and percent dry matter content and the flavor of the fruit is excellent, with a mild non-acid sweet taste.

The new cultivar is able to be asexually reproduced by softwood and hardwood cuttings or by budding or grafting onto a seedling or rooted cutting grown rootstock with stability through succeeding asexual propagations.

'AU Golden Dragon' is early blooming, very early maturing, yellow fleshed cultivar with high soluble solid contents, high percent dry matter and has very fine soft hairs on the brown skin surface.

Vegetative bud break on 'AU Golden Dragon' occurs around March 15-20, and the bloom period begins during the last week of March to the first week of April. The plant blooms over an extended period of about 14 days. 'AU Golden Dragon' average fruit maturity and harvest date is August 15-20, in contrast to 'AU Golden Sunshine' average fruit maturity and harvest date is September 10 and 'Hort 16A' (U.S. Pat. No. 11,066) average fruit maturity and harvest date is October 10. Fruit quality data was collected at harvest and after a 30 day cold treatment and fruit allowed to soften at room temperature (Table 1).

The percent soluble solids and dry matter content and the internal hue angle of the fruit flesh did not vary after the cold storage and softening periods. At harvest 'Hort 16A' (patented) had the highest percent soluble solids and 'AU Golden Dragon' had the lowest percent soluble solids, but there were no differences in percent dry matter content or internal hue angle. 'AU Golden Dragon' fruit has a total acidity (% citric acid) of 1.2.

Kiwi plants are dioecious and have vegetative and compound buds with flower clusters produced in the leaf axils of the first four to six nodes. Male and female flowers are perfect morphologically. The female flower contains some anthers but only the stigma is functional, whereas the flower on a male vine typically produces 125 to 185 large anthers that surround a small, vestigial stigma.

Kiwi buds enter endodormancy during winter, which requires a minimum number of chilling hours for maximum budbreak and bloom. Floral uniformity and density in spring is directly related to the amount of chilling received during winter. It is believed the more accurate measure of chilling hours is Richardson units, which are defined as the accumulated hours between 0° C. and 7° C. For maximum bud break and flowering of 'AU Golden Dragon' to occur, it was determined that 800 hours of chilling were required, and after the chilling requirement was met, 9500 growing degree hours were necessary for bud break. The low growing degree hours necessary for vegetative growth and bloom to occur results in the early growth and flowering of 'AU Golden Dragon' which in some years could result in damage from late spring frost. 'AU Golden Dragon' has performed well in central Alabama, which has an average winter chilling of 800-1200 hours.

'AU Golden Dragon' blooms earlier in the spring and its fruit ripens earlier in the fall than does 'Hort 16A' (patented). The first blooms open on 'AU Golden Dragon' were on March 30 and petal fall occurred about April 16-18. Open blooms were evident on 'Hort 16A' (patented) on April 8, and petal fall occurred about April 17. 'AU Golden Dragon' has an elliptical fruit shape in comparison to the ovoid fruit shape of 'Hort 16A' (patented). The stylar end of 'Hort 16A' (patented) has a much greater protrusion than does 'AU Golden Dragon'. Fruit of 'AU Golden Dragon' matures August 15-20 in comparison to the fruit of 'Hort 16A' (patented) maturing October 10.

DETAILED BOTANICAL DESCRIPTION

Figure 1:
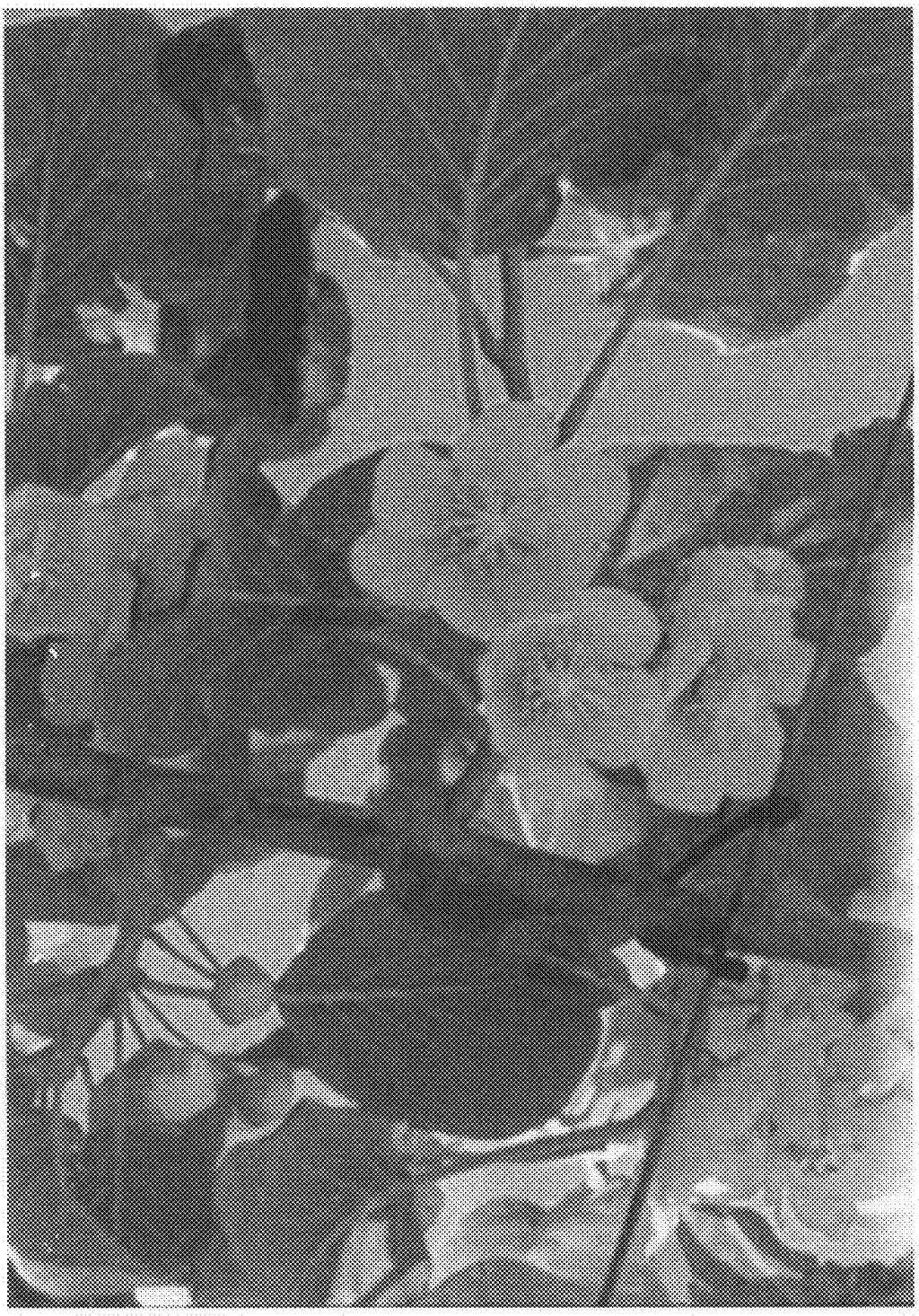
FIG. 1 is a photograph of 'AU Golden Dragon' bloom density on 8 year old plants.
Figure 2:
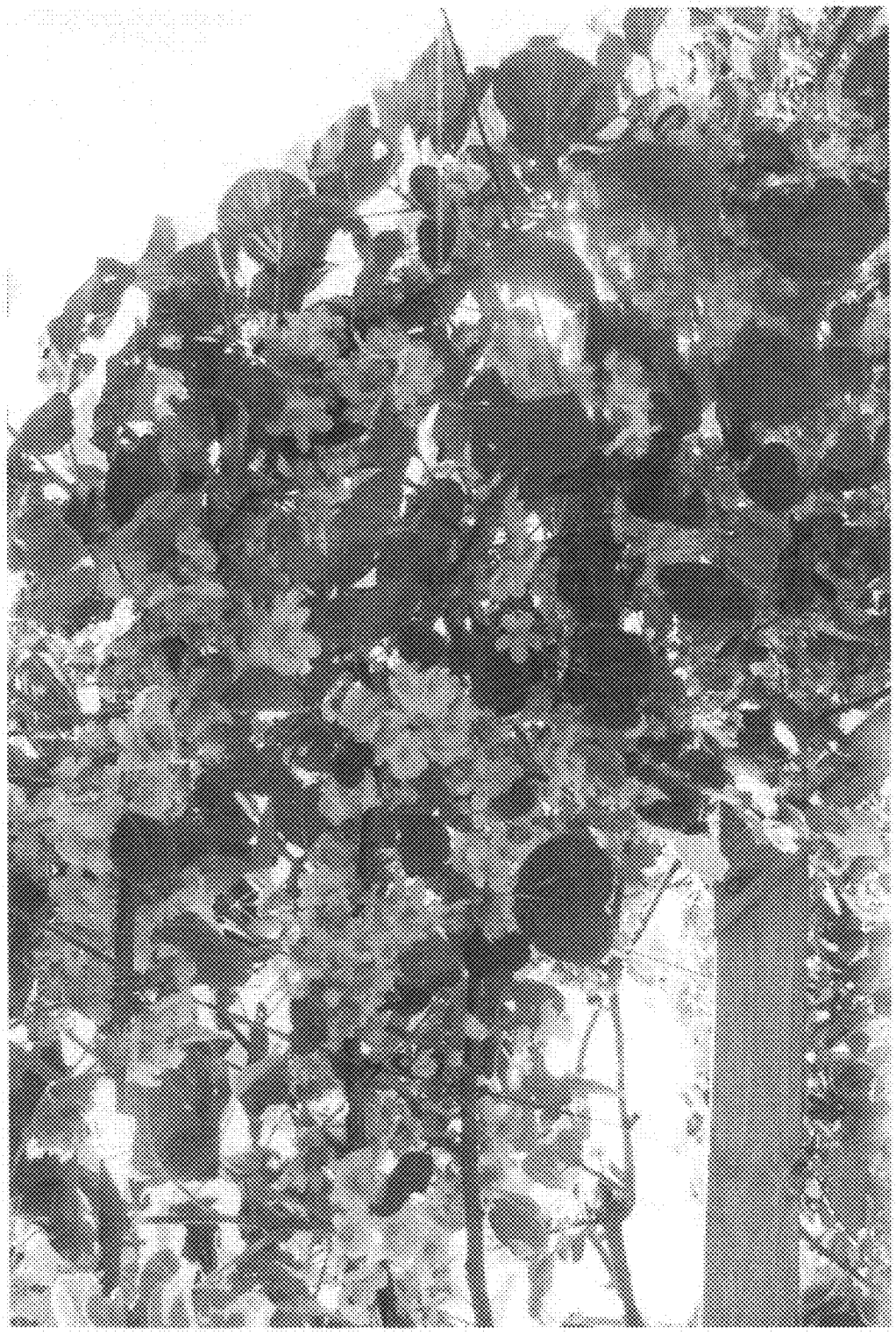
FIG. 2 is a photograph of 'AU Golden Dragon' in full bloomon 8 year old plants.
Figure 3:
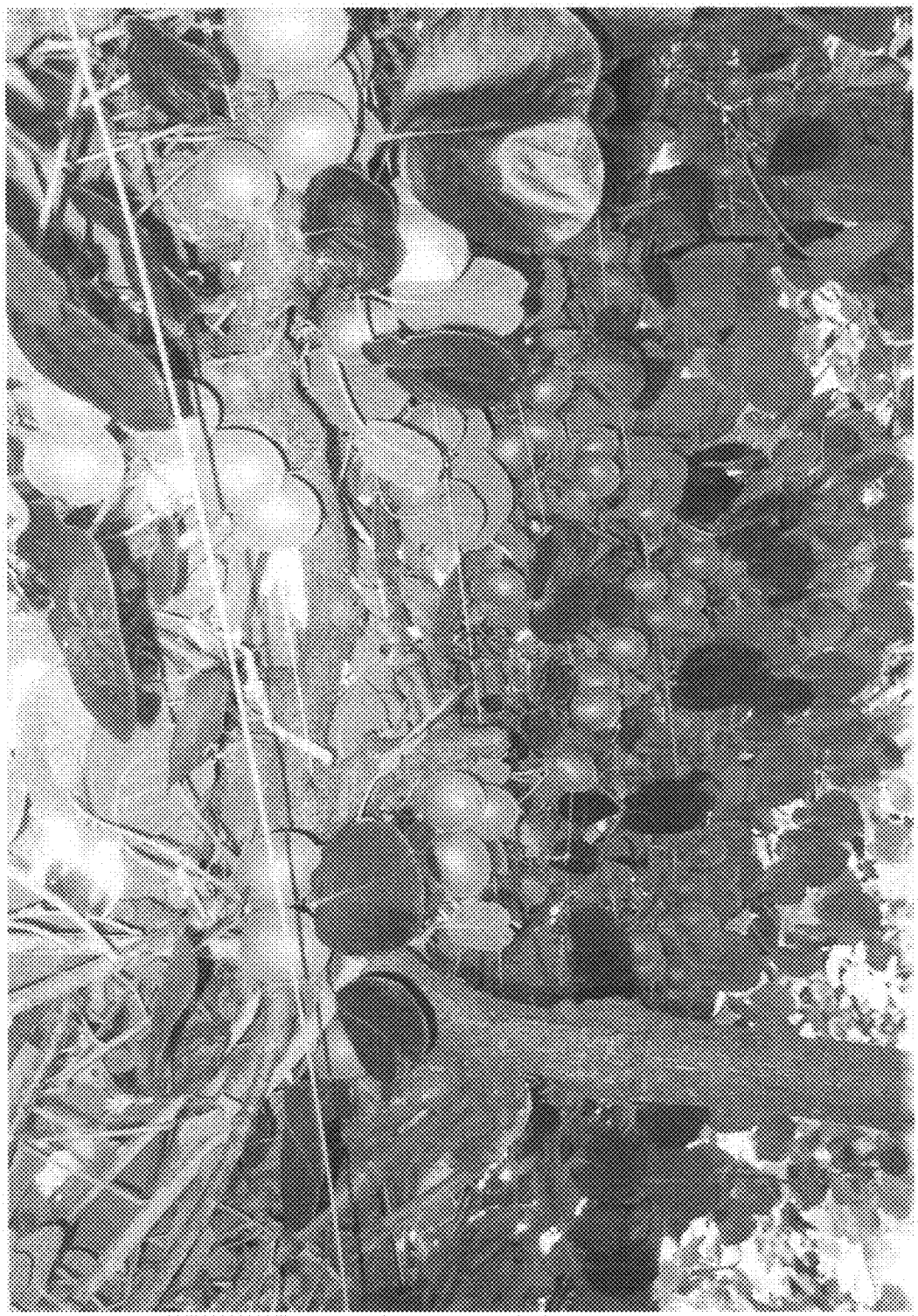
FIG. 3 is a photograph of 'AU Golden Dragon' vine crop load on 8 year old plants.
Figure 4:
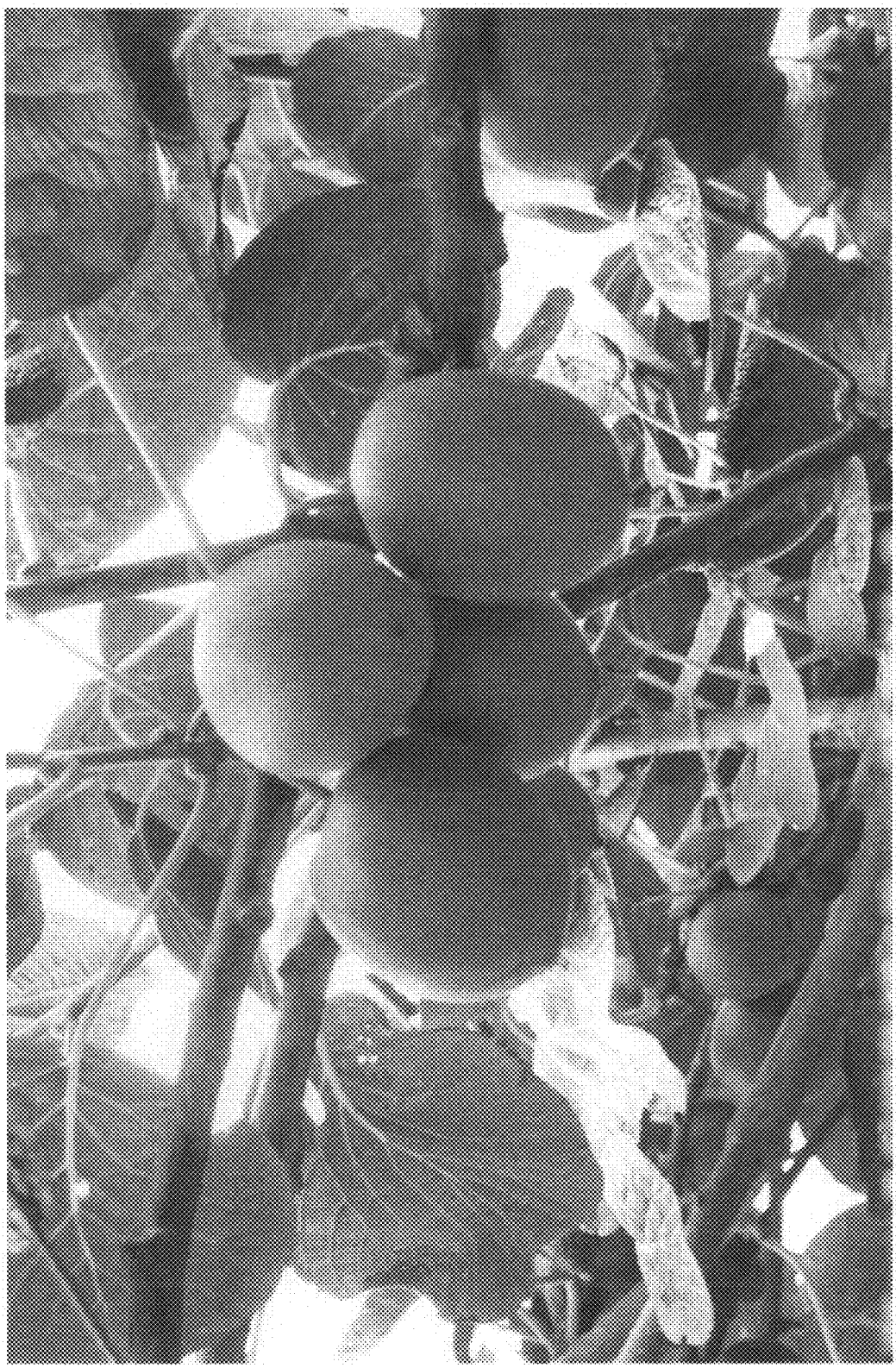
FIG. 4 is a photograph of 'AU Golden Dragon' individual fruit on vine on 8 year old plants.
Figure 5:
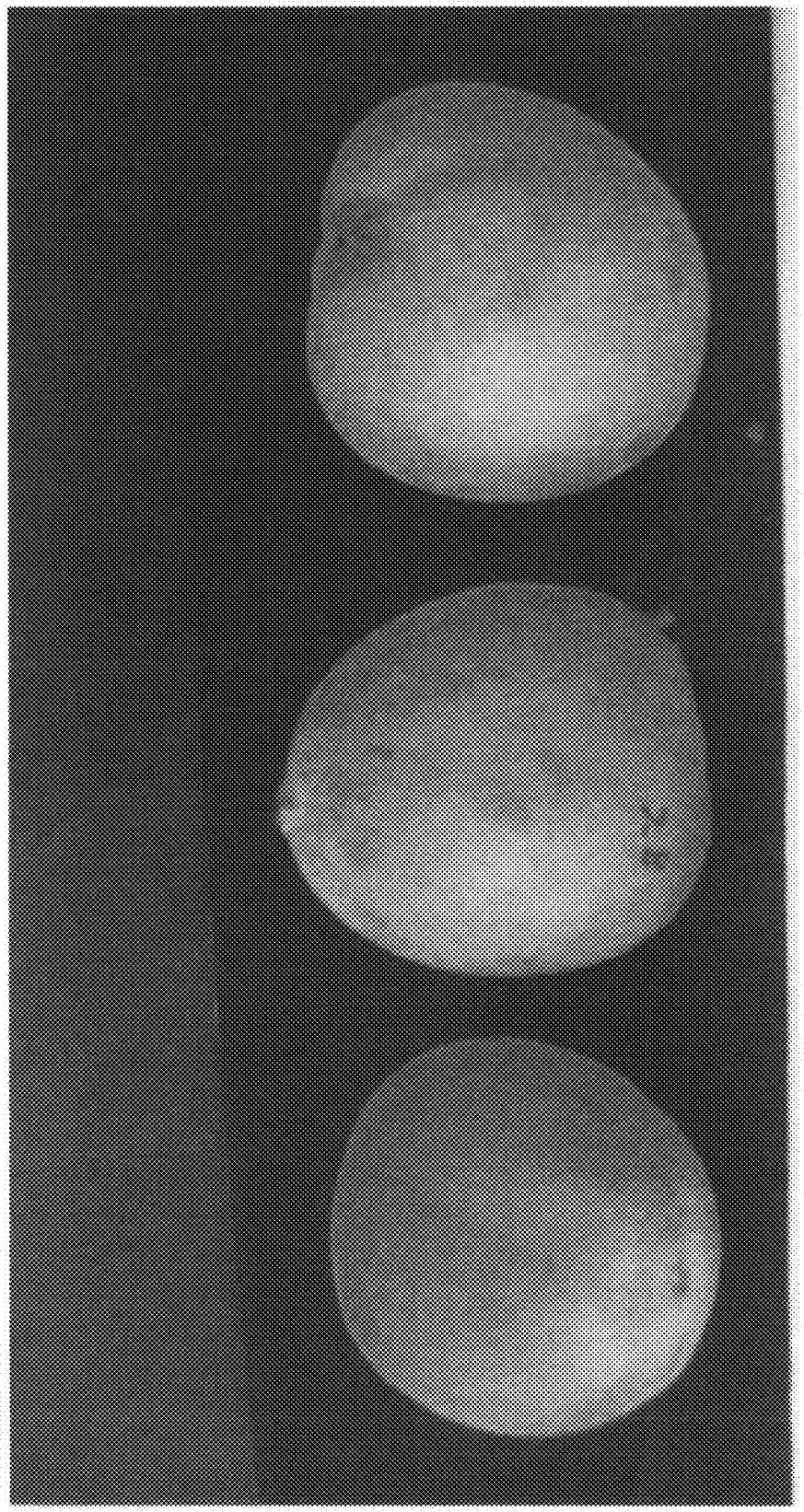
FIG. 5 is a photograph of 'AU Golden Dragon' fruit shape on 8 year old plants.
Figure 6:
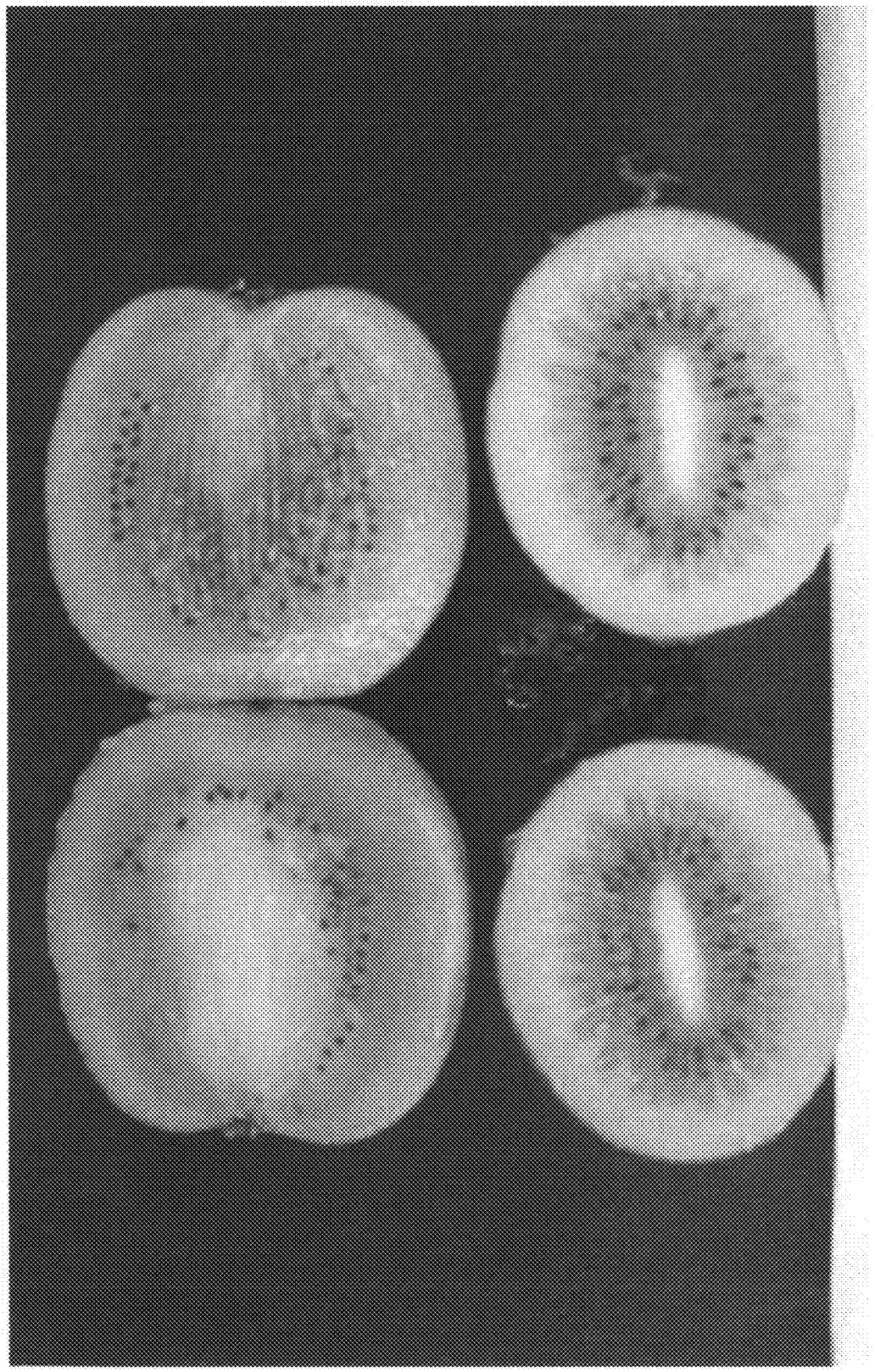
FIG. 6 is a photograph of 'AU Golden Dragon' flesh color.

Kiwi plants are large deciduous shrubs that originated in China and are dioecious, can climb up to 25 feet, and have alternate, broadly rounded petiolate leaves. The cream colored flowers that grow in axillary cymes mature into ovate to oblong fruits (berries) with brownish, hairy skins. There are over 50 species in the genus *Actinidia*. The two *Actinidia* species of the most commercial importance are *deliciosa* and *chinensis*. 'Hort 16A' (patented) is the most important yellow flesh *chinensis* cultivar in the commercial trade. The kiwi plant is dioecious thereby requiring male pollinizers in the presence of the female plants to ensure fruit production. The male and female plants bloom period has to be at the same time for pollination to occur. The bloom period varies with each cultivar depending upon the chilling requirement and the growing degree hour requirement after the chilling requirement has been met. *Actinidia* are temperate zone plants that prefer well drained moist and rich soil and grows as well in a sunny as in a half-shady position.

The new cultivar 'AU Golden Dragon' is pistillate, with imperfect flowers, e.g. the flowers produce only sterile pollen and thus require a pollinizer for fruit production. The male cultivar 'Hortkiwi Meteor' (not patented) bloom period occurs with 'AU Golden Dragon' bloom period and is the pollinizer used with 'AU Golden Dragon'. The bloom period of 'AU Golden Dragon' begins late March on average about March 28-30 which is 6-8 days before the bloom period of 'Hort 16A' (patented) begins.

The new cultivar is able to be asexually reproduced by softwood and hardwood cuttings or by grafting or budding onto a seedling or cutting grown rootstock with the unique characteristics coming true to form and are established and transmitted through succeeding asexual propagations. 'AU Golden Dragon' has been asexually propagated by rooting softwood and hardwood cuttings and grafting in China and Alabama.

The distinctive characteristics of this new kiwi cultivar described in detail below have been observed in field experiments in central Alabama and China. The 'Hort 16A' (patented) cultivar was evaluated in the same field experiments in Alabama and was used as the standard cultivar for comparison.

The general fruit shape of 'AU Golden Dragon' is elliptical whereas the general shape of 'Hort 16A' (patented) is ovoid. The fruit cross-section at medium is round with 'AU Golden Dragon' and is elliptic with 'Hort 16A' (patented). The general fruit shape at the stylar end is slightly protruding on 'AU Golden Dragon' in comparison to a very pronounced protrusion on 'Hort 16A' (patented). The fruit shape of the shoulder on the stalk end is rounded and flat on 'AU Golden Dragon' and rounded on 'Hort 16A' (patented).

'AU Golden Dragon' is the maternal parent of 'AU Golden Tiger' and is a companion and comparison fruiting cultivar to 'AU Golden Sunshine'. 'AU Golden Dragon' fruit matures 20 days before fruit of 'AU Golden Sunshine' and 50 days before fruit of 'Hort 16A' (patented). Fruit quality is very similar between the three female cultivars, 'AU Golden Dragon', 'AU Golden Sunshine' and 'Hort 16A' (patented), however they differ in bloom date, fruit maturity date, and fruit shape.

'AU Golden Dragon' is a good source of health promoting qualities such as vitamin C, antioxidant capacity, β carotene and total phenolics (Table 2).

Table 3 below illustrates the specific differences between the 'AU Golden Dragon' cultivar and the 'Hort 16A' (patented) cultivar from vines 6-14 years old.

TABLE 3

| | 'AU Golden Dragon' | 'Hort 16A' (patented) |
|---|---|---|
| Plant | | |
| Plant: sex expression | female (flowers imperfect) | |
| Plant: ploidy | diploid (2n = 2x = 58) | |
| Plant: vigor | strong | |
| Young shoot: hairs | present | |
| Young shoot: density of hairs | medium | |
| Young shoot: type of hairs | short | |
| Young shoot: anthocyanin coloration of growing tip | absent, N199B | |
| Young shoot: anthocyanin coloration of leaf axil | absent, N199B | |
| Plant: average height and spread | plant is a vigorous vine. They are grown on a trellis (either a T-bar or pergola trellis system) in which the plant is allotted a certain space of which it rapidly fills and is maintained in this space by both winter and summer pruning. The trellis is six feet off the ground and the plant is allowed each summer to grow and hang down on each side. | |
| Stem | | |
| Stem: coloration of leaf axil | absent, N199B | |
| Stem: diameter | | medium |
| Stem base diameter | mean 12.90 mm (range 10.01-16.46 mm) | mean 11.0 mm (range 8.3-13.3 mm) |
| Stem mid section diameter | mean 9.36 mm (range 7.26-11 mm) | not available |
| Stem: dormant bud diameter | 3.6 mm (2.8-4.67 mm) | 6.9 mm (4.9-8.3 mm) |
| Stem: color on upper side of shoot | grey brown, N199B | dark brown, 200B-200C-165A |
| Stem: character of bark | smooth | |
| Stem: hairs | present | |
| Stem: conspicuousness of lenticels | weak | conspicuous |
| Stem: number of lenticels | few | medium |
| Stem: color of lenticels | almond/ivory, 199D | brownish-white |
| Stem: size of bud support | medium | |
| Stem: visibility of bud (dormant canes) | visible | |
| Stem: number of hairs visible high on bud (dormant canes) | medium | |
| Stem: leaf scar | mean length 5.3 mm (3.6-6.1 mm) mean width 5.4 mm (4.2-6.5 mm) | medium |

TABLE 3-continued

| | 'AU Golden Dragon' | 'Hort 16A' (patented) |
|---|---|---|
| Leaf (Mature) | | |
| Leaf shape: | orbicular to broadly ovate | very broadly ovate |
| Leaf base shape: | cordate, lobes large, non- to cordate slightly overlapping | |
| Leaf tip shape: | rounded, with broad cuspidate tip | cuspidate |
| Leaf margin: | entire | ciliate |
| Leaf adaxial surface: | medium green; glossy, glabrous except sparse, unbranched hairs along main veins, 147A | light-medium green, medium glossiness, 146A |
| Leaf abaxial surface: | light green; dense, stellate pubescence everywhere except along veins which are densely tomentose with unbranched hairs, 147B | light green, 147B |
| Leaf length (cm): | 18.8 (15.6-24.8) | 17 (14.5-19.8) |
| Leaf width (cm): | 14.7 (11.9-16.9) | 18.6 (15.9-21.7) |
| Leaf ratio (l/w): | 1.3 (1.0-1.5) | |
| Leaf petiole length (cm): | 5.9 (4.4-8.7) | 16.7 (10-25) |
| Leaf 1° vein organization: | pinnate; veins terminating as small extended points or mucros at leaf margins | |
| Leaf 2° vein organization: | [ ]parallel | |
| Leaf puckering: | weak to moderate | weak |
| Leaf variegation: | none | |
| Leaf spines on lower leaf surface: | none; dense stellate hairs | |
| Petiole: | 147C | |
| Pedicel: | N199A | |
| Flower | | |
| Inflorescence: predominate number flower buds/stem | mean 4 (range 3-5) | mean 1.0 |
| 1° Pedicel length (cm): | 2.91 (2.1-3.4) | 4.2 (3.0-4.9) |
| 2° Pedicel length (cm): | n/a | n/a |
| Pedicel pubescence: | minutely, densely tomentose, unbranched | |
| Sepal#: | 6.7 (6-13) | >5 |
| Sepal color: | greyed-green to slightly rust colored at margin, 191B | |
| Sepal pubescence: | minutely, densely tomentose, unbranched | |
| Flower color: | creamy white, 155D | White, 155D |
| Flower width (cm): | 3.1 (2.8-3.5) | 1.8 (1.6-1.9) |
| Petal orientation: | distinctly overlapping: sides reflexing | overlapping |
| Petal #: | 6.6 (6-8) | 8 (6-10) |
| Petal length (cm): | 1.6 (1.4-1.8) | 2.3 (2.1-2.5) |
| Petal width (cm): | 1.2 (1.0-1.5) | 1.8 (1.6-1.9) |
| Petal ratio (l/w): | 1.3 (1.0-1.6) | 1.3 (1.1-1.5) |
| Ovary shape: | globose | |
| Ovary pubescence: | short, densely tomentose | strongly expressed |
| Style#: | 33 (28-38) | 30.85 (26 - 36) |
| Style orientation: | erect to spreading | erect |
| Stamen#: | 70.6 (65-78) | |
| Anther length (mm): | 2.0-2.5 | |
| Filament: | 155D | |
| Anther: | 169D | |
| Chilling requirement hours: | 800 | |
| Fruit | | |
| Fruit: average weight (g) | 88.2 (30.5-130.9) | 98.3 (43-176) |
| Fruit: length (mm) | 61.6 (48.8-73.0) | 79.1 (76.0-84.2) |
| Fruit: width (max) (mm) | 54.8 (46.3-61.7) | 53.1 (55.4-48.1) |

TABLE 3-continued

| | 'AU Golden Dragon' | 'Hort 16A' (patented) |
|---|---|---|
| Fruit: L/A ratio (max width) | 1.12 | 1.49 |
| Fruit: width (min) (mm) | 47.6 (40.8-52.3) | 49.1 (47.0-51.2) |
| Fruit: L/D ratio (min width) | 1.29 | 1.61 |
| Fruit: core diameter (max) (mm) | 18.6 (4.9-28.0) | 13.1 (9.1-17) |
| Fruit: core diameter (min) (mm) | 5.4 (2.5-15.8) | 4.9 (4.1-6.1) |
| Fruit: locule number | 29.7 (26-32) | 34.5 (26-37) |
| Fruit: peduncle length (mm) | 27.88 (19.11-33.81) | 48.3 (44.7-50.3) |
| Fruit: peduncle width (mm) | 1.95 (12-2.85) | 3.57 (3.2-4.3) |
| Fruit: general shape | elliptical | ovoid |
| Fruit: cross-section at median | round | elliptic |
| Fruit: general shape of stylar end | protruding | |
| Fruit: shape of shoulder on stalk end | rounded, flat | rounded |
| Fruit: skin color at harvest | Brown, N199A | yellow-brown |
| Fruit: skin color change during ripening | absent | yellow-brown |
| Fruit: skin color at maturity for consumption | Brown, N199A | combination of 199A plus 161A |
| Fruit: hairs | present | medium |
| Fruit: density of hairs | light | pubescent |
| Fruit: types of hairs | tomentose | |
| Fruit: hair length (mm) | short (0.05-0.12) | |
| Fruit: concentration of hairs | uniform | |
| Fruit: adherence of hairs to skin (when rubbed) | weak | |
| Fruit: core diameter (at largest diameter) | large (13.8 mm by 5.6 mm) | small |
| Fruit: core shape (in cross section) | elliptical | |
| Fruit: core woody spike | present | |
| Fruit: prominence of core woody spike | present | weak |
| Fruit: outer pericarp color at maturity for consumption | yellow green, 152C-152D | golden yellow, 12C-12B |
| Fruit: inner pericarp color (locules) at maturity for consumption | yellow green, 148A | brownish-yellow, 162A-162C |
| Fruit: core color at maturity | greyed-yellow, 160C | white, 159C |
| Fruit: seed color at maturity in flesh | dark brown, 200A | 200A |
| Fruit: seed color when dry | greyed-orange, 165D | brown, 200D |

Notes regarding Table 3:

1. Horticulture terminology is used in accordance with revised UPOV guidelines for kiwi.
2. Characters of comparison cultivar 'Hort 16A' (patented) are noted opposite that character when significantly different.
3. 'Hort 16A' (patented) plants were observed in the same study as the new cultivar.
4. All dimensions are in millimeters unless otherwise stated; weights are in grams.
5. The RHS 1966 color chart was used to determine actual color.

TABLE 1

Fruit Quality at harvest and after 30 days cold storage treatment of three *Actinidia chinensis* Planch golden kiwi cultivars grown in central Alabama and China.

| | Harvest[z] | | | |
|---|---|---|---|---|
| Cultivar | Firmness (Kg) | Soluble Solids (%) | Dry Matter (%) | Internal Hue Angle |
| 'Au Golden Dragon' | 4.4b[y] | 6.6c | 17.2 | 104 |
| 'AU Golden Sunshine' | 4.7b | 8.6b | 18.5 | 100 |
| 'Hort 16A' (patented) | | 5.8a | 11.7a | 21.0 |
| | 30 Days Cold Storage[x] | | | |
| Cultivar | Firmness (Kg) | Soluble Solids (%) | Dry Matter (%) | Internal Hue Angle |
| 'Au Golden Dragon' | 1.1 | 15.2 | 18.0 | 99 |
| 'AU Golden Sunshine' | 0.0 | 15.7 | 18.5 | 94 |
| 'Hort 16A' (patented) | 105 | 2.0 | 17.4 | 21.0 |

[z]Means derived from data taken in the 2006, 2008, 2009 and 2010 growing seasons. There was not fruit in 2007 due to a late spring frost killing flower buds.
[y]Mean separation within columns by Duncan's Multiple Range Test p = 0.05, columns without letters were not significantly different.
[x]Means derived from data taken in 2003, 2004, 2008, 2009 and 2010 for 'Au Golden Dragon' and 'AU Golden Sunshine" and in 2009 and 2010 for 'Hort 16A' (patented).

TABLE 2

Phytochemical properties of 'AU Golden Dragon' and 'AU Golden Sunshine' cultivars.

| Phytochemical properties | 'AU Golden Dragon' | 'AU Golden Sunshine' |
|---|---|---|
| Ascorbic acid (mg/100 g FW) | 96.98 | 94.43 |
| Vitamin C equivalent Antioxidant capacity (VCEA) | 161.60 | 177.90 |
| B carotene (mg/100 g FW) | 0.20 | 0.23 |
| Chlorophyll a (mg/100 g FW) | 0.11 | 0.12 |
| Chlorophyll b (mg/100 g FW) | 0.06 | 0.05 |
| Total Phenolics (mg GAE/100 g FW) | 135.70 | 155.50 |

What is claimed is:

1. A new and distinct variety of *Actinidia chinensis* Planch plant named 'AU Golden Dragon' substantially as described and illustrated herein.

* * * * *